US006565897B2

(12) United States Patent
Selvaraj et al.

(10) Patent No.: US 6,565,897 B2
(45) Date of Patent: *May 20, 2003

(54) EXTRACT OF NERIUM SPECIES, PHARMACEUTICAL COMPOSITION THEREOF AND METHODS FOR PREPARATION THEREOF

(75) Inventors: Ulagaraj Selvaraj, San Antonio, TX (US); Chandra U. Singh, San Antonio, TX (US); Huseyin Z. Ozel, Istanbul (TK)

(73) Assignee: Ozelle Pharmaceuticals, Inc., San Antonio, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/401,494

(22) Filed: Sep. 22, 1999

(65) Prior Publication Data

US 2002/0114852 A1 Aug. 22, 2002

(Under 37 CFR 1.47)

Related U.S. Application Data

(60) Provisional application No. 60/101,622, filed on Sep. 24, 1998.

(51) Int. Cl.$^7$ .......................... A01N 65/00; A61K 35/78
(52) U.S. Cl. ........................................................ 424/725
(58) Field of Search ............................. 424/195.1, 725

(56) References Cited

U.S. PATENT DOCUMENTS 5,135,745 A    8/1992   Ozel

FOREIGN PATENT DOCUMENTS

DE         0398313      11/1990   ............ C08B/37/00

*Primary Examiner*—Herbert J. Lilling
(74) *Attorney, Agent, or Firm*—Katten Muchin Zavis Rosenman

(57) ABSTRACT

A substantially sterile extract of Nerium species is described, together with a method for production thereof. A pharmaceutical composition comprising the extract is also described, together with a method for production thereof. The pharmaceutical composition is useful for the treatment of cell-proliferative and immune deficient diseases in mammals, including cancer and AIDS, respectively.

40 Claims, No Drawings

EXTRACT OF NERIUM SPECIES, PHARMACEUTICAL COMPOSITION THEREOF AND METHODS FOR PREPARATION THEREOF

RELATED APPLICATION

This patent application claims the priority date of United States provisional patent application S. No. 60/101,622, filed Sep. 24, 1998, the contents of which are hereby incorporated by reference.

BACKGROUND OF THE INVENTION

1. Field of the Invention

In one of its aspects, the present invention relates to an extract of a species of Nerium, particularly *Nerium Oleander*, and to a method for production thereof. In another of its aspects, the present invention relates to a pharmaceutical composition comprising an extract of a species of Nerium, particularly *Nerium Oleander*, and to a method for production thereof. The pharmaceutical composition is useful, inter alia, in the treatment of the cell-proliferative and immune deficient diseases in mammals, including cancer and AIDS.

2. Description of the Prior Art

A variety of herbal and plant extracts or preparations are available for mankind for treating any number of diseases affecting the human body [1, 4]. U.S. Pat. No. 4,986,895 [Grossman et al.] teaches the use of water soluble plant extracts in the treatment of virus skin infections. U.S. Pat. No. 5,178,865 [Ho et al.] teaches the use of Chinese herbal extracts in the treatment of HIV related disease in vitro. U.S. Pat. No. 5,482,711 [Medenica] teaches the use of the extract of the plant *Nigella Sativa* in the treatment of cancer, viral diseases and protection from side effects of chemotherapy. Many cell anti-proliferative agents are natural products of fungi, plants and marine animals, and these materials are likely to be the primary sources for anti-proliferative agents for the future. Examples of this class of agents include taxol, vincristine and camptothecin.

U.S. Pat. No. 5,135,745 [Ozel, 20], the contents of which are hereby incorporated by reference, teaches the use of the extract of the plant *Nerium Oleander* for the treatment of cell proliferation diseases in animals and humans. Ozel [20] teaches preparing the water extract of the plant *Nerium Oleander* and administering the extract to human subjects in order to ameliorate cell-proliferative diseases such as cancer. As used throughout this specification, the term "cell-proliferative disease" is intended to mean malignant as well as non-malignant cell populations which often appear morphologically to differ from the surrounding tissue. Ozel [20] teaches a screen to be used in determining whether a particular patient would be a suitable candidate to receive a therapeutic regimen of the extract. Specifically, Ozel [20] teaches initial adminstration of an injectable form of the extract following by observation to detect the onset of fever (from about 38° C. to about 41° C.) in the patient. If the fever develops, the patient is deemed to be a suitable candidate for receiving a therapeutic regimen of the extract. Thus, Ozel [20] teaches a nexus between efficacy of the extract and the onset of a fever in the patient during the screening. In other words, Ozel teaches that a patient who fails to develop a fever during the screening will not be a suitable candidate for receiving a therapeutic regimen of the extract.

The plant oleander is a well-known ornamental plant with leathery evergreen leaves and handsome clusters of red or pink or white flowers. The plant originates from the Mediterranean region and is indigenous to the Indo-Pakistan subcontinent. The plant grows as a weed in the southern part of Texas. In the Mediterranean region, the plant previously has been used for a variety of medicinal purposes. For example: (i) the macerated leaves have been used to relieve itchiness and help prevent hair from falling out, (ii) fresh leaves have been applied to treat tumors, (iii) the decoction of leaves and bark has been used to treat syphillis, and (iv) the decoction of leaves has been used as a gargle to strengthen the teeth and gums and as a nose drop for children [1–4].

Oleander is one of the digitalis-like plants. The plant has certain toxic properties due to the presence of digitoxin like steroidal glycosides. It is estimated that as many as 100 chemical substances are present in various parts of the Oleander plant. Various of the compounds that have been identified in *Nerium Oleander* set out in Table 1.

Ozel describes a procedure for the preparation of *Nerium Oleander* Extract (NOE) in water [20, 21]. The specific extraction of the plant *Nerium Oleander* taught by Ozel [20, 21] involves, cooking the leaves and stems of the plant in water for 2–3 hours and filtering off the residues. Some of the chemical constituents have been separated from the aqueous extract and have been analyzed [22]. The extract has been found to comprise several polysaccharides with very potent immune stimulating properties. The various polysaccharides identified in the aqueous NOE set out in Table 2. These polysaccharides can be mixed with various pharaceutically acceptable carriers to form injectables, capsules, tablets and various other administrative forms [22].

TABLE 1

CHEMICAL COMPOUNDS IDENTIFIED IN NERIUM OLEANDER

| No. | Compound Name | Type | Reference |
|---|---|---|---|
| 1 | Oleandrin | Steroid | [5] |
| 2 | Adynerin | Oleanane | [6] |
| 3 | Ursolic Acid | Oleanane | [6] |
| 4 | Kaneric Acid | Oleanane | [7] |
| 5 | Neriucoumaric Acid | Oleanane | [8] |
| 6 | Oleanderen | Oleanane | [9] |
| 7 | Oleanderol | Oleanane | [10] |
| 8 | Kamerin | Oleanane | [17] |
| 9 | Dihydroursolic Acid | Oleanane | [18] |
| 10 | Kanerocin | Oleanane | [19] |
| 11 | Oleanderolic Acid | Oleanane | [11] |
| 12 | Kanerodione | Oleanane | [11] |
| 13 | Kaneroside | Oleanane | [12] |
| 14 | Neriumoside | Oleanane | [12] |
| 15 | cis-Karenin | Oleanane | [13] |
| 16 | trans-Karenin | Oleanane | [13] |
| 17 | Pregnane Saponins | Steroids | [14–16] |
| 18 | Cardenolides Saponins | Steroids | [14–16] |

TABLE 2

CHEMICAL CONSTITUENTS OF NERIUM OLEANDER EXTRACT

| No. | Poly-saccharide | Type & Sugars | Molecular Wt. |
|---|---|---|---|
| 1 | PS-I | Poly α (1→4) D-Galacturonic Acid | 30,000–40,000 |
| 2 | PS-II | Branched polymer D-Galacturonic Acid Arabinose, Rhamnose Galactose, Xylose Glucose | 10,000–12,000 |

TABLE 2-continued

CHEMICAL CONSTITUENTS OF
NERIUM OLEANDER EXTRACT

| No. | Poly-saccharide | Type & Sugars | Molecular Wt. |
|---|---|---|---|
| 3 | PS-III | Branched polymer D-Galacturonic Acid Arabinose, Rhamnose Galactose, Xylose Glucose | 5,000–6,000 |
| 4 | PS-IV | Branched polymer D-Galacturonic Acid Arabinose, Rhamnose Galactose, Xylose Glucose | 2,500–3,500 |

While the extract taught by Ozel [20] is a significant advance in the art of treatment of cell-proliferative diseases in humans, there is still room for improvement. Specifically, as described above, Ozel [20] teaches that only patients who develop a fever during the screening procedure are suitable canditates to receive a therapeutic regimen of the extract. Further, there are technical problems in producing the extract in a commercially suitable form for parenteral administration using the process taught by Ozel [20]. In particular, there is a problem regarding the stability, sterility and endotoxin level of the extract during extended periods of use on human subjects. The aqueous NOE extract described in Ozel [20] is relatively unstable at room temperature over any significant period of time. In particular, the aqueous extract described in Ozel [20], loses its potency when stored at ambient temperatures.

Accordingly, it would be desirable to have an improved extract of the Nerium species which could be used with patients who do not develop a fever during initial screening. It would also be desirable if the extract itself had improved stability and could be used to produce a formulation of improved stability.

SUMMARY OF THE INVENTION

It is an object of the present invention to provide a novel extract of a species of Nerium which obviates or mitigates at least one of the above-mentioned disadvantages of the prior art.

It is another object of the present invention to provide a novel process for producing an extract of a species of Nerium.

It is yet another object of the present invention to provide a novel pharmaceutical composition which obviates or mitigates at least one of the above-mentioned disadvantages of the prior art.

It is yet another object of the present invention to provide a novel process for producing a pharmaceutical composition.

Accordingly, in one of its aspects, the present invention provides a substantially sterile extract of Nerium species.

In another of its aspects, the present invention provides a method for producing a substantially sterile extract of Nerium species, the method comprising the steps of:
(i) dispersing plant matter of the Nerium species in water;
(ii) heating the dispersed plant matter for at least about 1.0 hour;
(iii) separating the heated water from the plant matter to produce a crude extract; and
(iv) sterilizing the crude extract to produce the substantially sterile extract of Nerium species.

In yet another of its aspects, the present invention provides a pharmaceutical composition comprising a substantially sterile extract of Nerium species, together with at least one pharmaceutically acceptable excipient therefor.

In yet another of its aspects, the present invention provides a process for producing a pharmaceutical composition comprising the steps of:
(i) mixing a substantially sterile extract of Nerium species with at least one pharmaceutically acceptable excipient and water;
(ii) drying the mixture produced in Step (i).

In yet another of its aspects, the present invention provides a novel pharmaceutical composition for the treatment of cell-proliferative and immune deficient diseases in mammals, including cancer and AIDS, respectively. The pharmaceutical composition comprises a therapeutically effective amount of a substantially sterile extract from a species of Nerium, preferably made according to the process described below.

In yet another of its aspects, the present invention provides a novel pharmaceutical composition for pain remediation in mammals. The pharmaceutical composition comprises a therapeutically effective amount of a substantially sterile extract from a species of Nerium, preferably made according to the process described below.

While specific reference will be made in this specification to Nerium oleander extract (NOE), those of skill in the art will appreciate that the present invention may be applied to various species of the the Nerium genus. For the sole purpose of convenience and ease of understanding, reference is made in the illustrative embodiments to NOE.

In a further aspect of the present invention there is provided a dried NOE powder suitable for use as a pharmaceutical composition. This powder is stable for at least approximately 3 to 5 years. The NOE powder may be freeze-dried, dried by heating and evaporation or spray-dried. The NOE powder of known quantity may be mixed with required excipients and water to form an aqueous solution comprising NOE which in turn is dried to form a powdered pharmaceutical composition which is also stable for at least approximately 3 to 5 years. The powdered pharmaceutical composition can then be quickly reconstituted with water prior to administration to form a clear solution. This solution is stable for a period of approximately one month.

In yet another of its aspects, the present invention provides a method for making a freeze-dried pharmaceutical composition comprising a therapeutically effective amount of NOE which is stable for at least 3 to 5 years. The method for making a freeze-dried pharmaceutical composition comprising a therapeutically effective amount of NOE comprises the steps of.
(i) mixing a NOE powder with the desired excipients and dissolving in water; maintaining the pH of the solution in the range of from about 5 to about 8, preferably from about 6 to about 7;
(ii) filtering the solution with filter having an average pore size of less than about 1.0 μm for sterilization; and
(iii) freeze-drying the solution under sterile conditions.

Preferably, freeze-drying is conducted in individual enclosures (e.g., vials) which are then sealed under the original vacuum in the freeze-drying compartment and can be reconstituted for use on human subjects whenever necessary. Thus, the present invention provides a means to produce a pharmaceutical composition containing a required amount of NOE powder.

In yet another of its aspects, the present invention provides a pharmaceutical topical cream comprising an amount of an NOE powder therapeutically effective for treating cell-proliferative diseases in mammals, together with a suitable exciptient therefor. Preferably, the excipient comprises an oil-in-water, semi-solid dosage form. A particularly preferred embodiment of such an excipient is discussed hereinbelow.

In a further aspect of the present invention there is provided a method of treating a mammal using a suitable pharmaceutical composition as described herein.

A number of different excipients may be used in the compositions of the present invention. These will be discussed in more detail hereinbelow.

In yet another of its aspects, the present invention provides a pharmaceutically acceptable parenteral preparation of NOE suitable especially for intramuscular or subcutaneous injections in human or animal subjects. The NOE product manufactured using the present invention is highly suitable for commercial shipping, handling and storing under ambient temperature. The product manufactured based on the present invention is stable at ambient temperature for at least up to 3 to 5 years. Thus, this aspect of the present invention may be used to manufacture commercial quantities of vials containing NOE.

Further objects, features and advantages of the invention will be apparent from the following detailed description when taken in conjunction with the accompanying Tables.

DETAILED DESCRIPTION OF THE PREFERRED EMBODIMENTS

Thus, an aspect of the present invention relates to a substantially sterile extract of Nerium species. As used throughout this specification, the term "substantially sterile", when used in conjunction with an extract of Nerium species, is intended to mean an extract which meets the requirements under the "Sterility Tests" as described in the United States Pharmacopeia, The National Formulary, USP 23, NF 18, USP, pgs. 1686–1690, Rockville, Md. (1995), the contents of which are hereby incorporated by reference. In this regard, it should be noted that the extract taught by Ozel [20] does not meet these requirements.

Preferably, the concentration of bacterial endotoxins in the present extract is less than about 300 units/mL, preferably in the range of from about 20 units/mL to about 150 units/mL, more preferably in the range of from about 20 units/mL to about 120 units/mL, even more preferably in the range of from about 20 units/mL to about 100 units/mL, even more preferably in the range of from about 20 units/mL to about 80 units/mL, most preferably from about 20 units/mL to about 50 units/mL.

The determination of the concentration of bacterial endotoxins in the extract is within the purview of a person of ordinary skill in the art. Preferably, the concentration of bacterial endotoxins in the extract may be determined by performing a conventional Limulus Amebocyte Lysate (LAL) Test as set out in the United States Pharmacopeia, The National Formulary, USP 23, NF18, USP, pgs. 1696–1697, Rockville, Md. (1995), the contents of which are hereby incorporated by reference.

The species of Nerium useful to produce the present extract is not particularly restricted. For example, three Nerium species, *Nerium Indicum, Nerium Oleander* and *Nerium Odorum,* may be found in various regions from the Mediterranean to Japan. Preferably, the species of Nerium used in the present invention is *Nerium Oleander,* also known as pink oleander and belonging to the Apocynceae family. As is known, pink oleander is a shrub that grows about 8–12 feet tall with leathery long leaves about 9 inches long and 1 inch wide. The shrub flowers in red, pink, white or cream colored clusters from spring to fall. All parts of the plant, including the leaves, flowers and twigs contain cardiac glycosides such as oleandrin, neriin, folinerin, digitoxigenin and nerigoside.

The physical form of the substantially sterile extract of the present invention is not particularly restricted. In one embodiment, the extract is in a liquid, preferably aqueous, form. In another embodiment, the extract is in a solid, preferably powedered, form. If the extract is in a powdered form, preferably, it is prepared by drying a liquid composition comprising the extract.

The specific drying technique is not particularly restricted provided that it does not adversely affect the active constituents of the extract. Non-limiting examples of useful drying techniques include: lyophilization (freeze-drying), spray-drying and evaporation of the solution under reduced pressure.

The lyophilization method is the preferred method for the preparation of NOE powder because the chemical entities, including the polysaccharides, present in the extract solution are well preserved with respect to the molecular structure which is essentially not altered during the drying process under sub-zero conditions. The preparation of the NOE powder by lyophillization is described in detail in Example 1 hereinbelow. In the lyophillization process, the NOE solution is normally frozen rapidly in stainless steel metal tray containers placed in the shelf of the freeze-dryer which is kept at a temperature in the range of from about −35° C. and about −40° C. The frozen solution is then lyophilized and a fluffy dry powder results from the removal of water by freeze-drying. This NOE powder may be stored for extended periods under conditions that reduce chemical degradation of the constituents or the absorption of moisture by the extract solution. Examples of such conditions include powder sealed under an atmosphere of dry, inert gas (such as argon, nitrogen, etc.) and storage below zero degree centigrade. Further, the lyophilized NOE powder can be readily dissolved in pyrogen-free deionized water or any other form of water suitable for injection to produce the extract without any significant loss of its biological potency.

The NOE powder can also be prepared by a conventional spray-drying technique. Spray drying is a process of converting a liquid into a powder by spraying the liquid into a hot drying gaseous medium. This process constitutes: (1) generation of liquid aerosol droplets, (2) evaporation of solvent from these droplets resulting in solution supersaturation, and (3) nucleation and precipitation of the supersaturated solution within the droplets.

The present substantially sterile extract of Nerium species may produced by a method comprising the steps of:
(i) dispersing plant matter of the Nerium species in water;
(ii) heating the dispersed plant matter for at least about 1.0 hours;
(iii) separating the heated water from the plant matter to produce a crude extract; and
(iv) sterilizing the crude extract to produce the substantially sterile extract of Nerium species.

The production of the crude extract (i.e., Steps (i), (ii) and (iii)) is generally similar to the technique disclosed in U.S. Pat. No. 5,135,745 [Ozel, 20], the contents of which are hereby incorporated by reference.

Preferably, Step (ii) is conducted at a temperature of at least about 40° C., more preferably in the range of from about 70° C. to about 120° C., even more preferably in the range of from about 80° C. to about 110° C., most preferably in the range of from about 90° C. to about 100° C.

Preferably, Step (ii) is conducted for a period in the range of from about 1 to about 24 hours, more preferably from about 1 to about 10 hours, most preferaby from about 1 to about 5 hours.

Step (iv) serves to convert the crude extract to a substantially sterile extract. This may be accomplished, for example, by filter sterilization of the crude extract using the procedure for sterile filtration set out in USP Monograph (USP 23<71>), the contents of which are hereby incorporated by reference. Preferably, the curde extract is converted to a substantially sterile extract by passing the crude extract through a filter having an average porosity of less than about 1 $\mu$m, more preferably less than about 0.8 $\mu$m, even more preferably less than about 0.5 $\mu$m, most preferably less than about 0.2 $\mu$m.

During Step (iv), the concentration of endotoxins in the crude extract is reduced to a value less than about 300 units/mL, preferably in the range of from about 20 units/mL to about 150 units/mL, more preferably in the range of from about 20 units/mL about 120 units/mL, even more preferably in the range of from about 20 units/mL to to about 100 units/mL, even more preferably in the range of from about 20 units/mL to about 80 units/mL, most preferably from about 20 units/mL to about 50 units/mL.

In a preferred embodiment of the method, the crude extract is subject to a further heating step prior to Step (iv). The duration and temperature of this additional heating step may be selected from the preferred embodiments of the Step (ii) discussed hereinabove.

The product obtained by this method is a substantially sterile extract of Nerium species which, together with at least one pharmaceutically acceptable excipient, may be formulated into a pharmaceutical composition. While the active substances in the extract can be administered alone, it is generally preferred that they be administered with at least one pharmaceutically acceptable excipient, the latter selected on the basis of the chosen route of administration and standard pharmaceutical practice. The term "pharmaceutically acceptable excipient" is intended to mean an ingredient used in a pharmaceutical preparation which does not function as an active agent.

Thus, the present pharmaceutical composition may be formulated oral, topical, rectal, parenteral, local, inhalant, topical or intracerebral administration. In an embodiment of the invention, the substances are administered in intranasal form via topical use of suitable intranasal vehicles, or via transdermal routes, using forms of transdermal skin patches known to those of ordinary skill in that art. To be administered in the form of a transdermal delivery system, the dosage administration will be continuous rather than intermittent throughout the dosage regimen. The substances can also be administered by way of controlled or slow release capsule system and other drug delivery technologies.

Thus, the present substantially sterile extract of Nerium species is typically administered in admixture with suitable pharmaceutical diluents or carriers suitably selected with respect to the intended form of administration, that is, oral tablets, capsules, elixirs, syrups and the like, consistent with conventional pharmaceutical practices.

For example, for oral administration in the form of a tablet or capsule, the active substances can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and coloring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like.

Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and flavouring agents to increase patient acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl-paraben, and chlorobutanol.

The substantially sterile extract of the invention can also be administered topicially, for example, in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

A particuarly preferred form of topical administration of the present substantially sterile extract of the invention is via a cream composition. Preferably, the composition is formulated in an oil-in-water, semi-solid dosage form. In this case, the active ingredient (i.e., the substantially sterile extract of Nerium species), may be formulated in a moisturizing base that has beneficial effect on its own.

A preferred cream-based formulation comprises: (i) emulsifying, defoaming and thickening agents, (ii) an antioxidant, (iii) an emollient humectant, (iv) preservatives/antimicorbial agents (optional), and (v) a diluent (optional).

Non-limiting examples of suitable emulsifying, defoaming and thickening agents may be selected from the group comprising Meezawax™, glyceryl monostearate, cetyl alcohol, polyoxy 50 stearate, Tween™ 20, petrolatum lanolin alcohol, liquid lanolin and mixtures thereof. Preferably, these agents may be used in an amount of up to about 40%, preferably in the the range of from about 10% to about 40%, by weight of the composition. A non-limiting example of a suitable antioxidant is vitamin E acetate. Preferably, the antioxidant is used in an amount of up to about 5%, preferably in the the range of from about 1% to about 3%, by weight of the composition.

A non-limiting example of a suitable emollient humectant is glycerin. Preferably, the emollient humectant is used in an amount of up to about 15%, preferably in the the range of from about 5% to about 10%, by weight of the composition.

The emulsifying, defoaming and thickening agents, antioxidant and emollient humectant make up a cream base which facilitates application of the active ingredient to the skin.

It is known in the art to add preservatives/antimicorbial agents to cream formulations to improve the shelf life of the formulation. Non-limiting examples of suitable such agents may be selected from the group comprising methyl paraben, propyl paraben, potassium sorbate and mixtures thereof. If present, it is preferred to use methyl paraben in an amount of up to about 0.3%, preferably in the the range of from about 0.05% to about 0.2%, by weight of the composition. If present, it is preferred to use propyl paraben in an amount of up to about 0.03%, preferably in the the range of from about 0.005% to about 0.02%, by weight of the composition. If present, it is preferred to use potassium sorbate in an amount of up to about 0.3%, preferably in the the range of from about 0.01% to about 0.2%, by weight of the composition.

A non-limiting example of a suitable diluent is de-ionized water which also has some moisturizing properties.

The substantially sterile extract of the invention may also be coupled with soluble polymers which are targetable drug carriers. Examples of such polymers include polyvinylpyrrolidone, pyran copolymer, polyhydroxypropylmethacrylamide-phenol, polyhydroxyethylaspartamidephenol, or polyethyleneoxide-polylysine substituted with palmitoyl residues. The extract may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxybutyric acid, polyorthoesters, polyacetals, polydihydropyrans, polycyanoacylates, and crosslinked or amphipathic block copolymers of hydrogels. The extract may also be affixed to rigid polymers and other structures such as fullerenes or Buckeyballs.

Suitable pharmaceutical carriers and methods of preparing pharmaceutical dosage forms are described in *Remington's Pharmaceutical Sciences* (Mack Publishing Company), the British Pharmacopeia, the Japanese Pharmacopeia, the United States Pharmacopeia XXII and the National Formulary XVII and supplements thereto, each of which is standard reference text in this field, and the contents of each of which are hereby incorporated by reference.

A preferred antioxidant excipient is a substance, which is added to a pharmaceutical preparation, inhibits oxidation and deterioration of the pharmaceutical preparation by oxidative processes. Such processes include the development of rancidity in oils and fats or the inactivation of some medicinals in the environment of their dosage forms. Non-limiting examples of antioxidants suitable for injection include ascorbic acid, sodium ascorbate, sodium bisulfate, sodium metabisulfate, DL-alpha-Tocopherol, monothioglycerol and mixtures thereof. In addition, there are other chemical agents available for use as antioxidants in a pharmaceutical preparation.

A preferred preservative excipient is a substance that prevents or inhibits microbial growth and may be added to a pharmaceutical preparation for this purpose to avoid consequent spoilage of the preparations by microorganisms. Non-limiting examples of suitable anti-microbial preservatives include methylparaben, methylparaben sodium, propyl paraben, propyl paraben sodium, ethylparaben, butylparaben, benzoic acid, sodium benzoate, potassium benzoate, phenylmercuric acetate, phenylmercuric nitrate, potassium sorbate, benzalkonium chloride, benzthonium chloride and mixtures thereof.

The present pharmaceutical composition may contain, inter alia, solubilizer excipients or surfactant excipients suitable for injection. Non-limiting examples thereof include various Tween™ products such as Tween™ 80, Tween™ 20, Tween™ 40, Tween™ 60, lecithin, sodium lauryl sulfate and mixtures thereof.

The present pharmaceutical composition may be produced by a process comprising comprising the steps of:
 (i) mixing a substantially sterile extract of Nerium species with at least one pharmaceutically acceptable excipient and water;
 (ii) drying the mixture produced in Step (i).

Step (i) may be accomplished by dissolving a previously dried sample of substantially sterile extract of Nerium species in a suitable solvent and adding the excipient(s) thereto. Alternatively, it may be possible to use the product of the process to produce the extract direcly in Step (i) of this process. The relative amount of extract used in Step (i) may vary depending on the amount of excipients added and the type of cell-proliferative diseases to be treated with the pharmaceutical composition. Preferably, the extract is used in the form of NOE powder, more preferably in an amount in the range of from about 0.01 mg/mL to about 100 mg/mL, most preferably in the range of from about 1 mg/mL to about 30 mg/mL. Antioxidants, preservatives and other any other desirable excipients may be added with or subsequent to adding the NOE powder.

The resulting solution may be sterilized using any of the known methods appropriate to preserving the active constituents. The preferred method of sterilizing the resulting solution is by filtering through a micron filter as discussed hereinabove using sterile equipment and techniques. Alternatively, the components of the pharmaceutical composition may be sterilized by any of the known methods appropriate to preserving the active compound prior to mixing in water and may be mixed using sterile equipment and technique. The sterile filtering method is preferred for the pharmaceutical composition of the present invention because the active constituents will not be destroyed by the process. For example, the solution may be dispensed in a sterile container (e.g., a vial) under sterile conditions, lyophilized and capped under original vacuum. Prior to use, the lyophilized pharmaceutical preparation can be reconstituted for injection using water suitable for injection.

The pharmaceutical composition of the present invention is relatively non-toxic. For example, the $LD_{50}$ value of the pharmaceutical composition containing 15 mg/mL by intravenous injection in mice is more than 4 mL/kg. It is well documented in the scientific literature that polysaccharides derived from plants, fungi, bacteria, algae and marine weeds a have wide range of biological activities, including, anti-tumor [24–28], immunological [29–32], anti-complimentary [33–37], anti-inflammatory, anti-coagulant, hypoglycemic [41–43] and anti-viral [44–45] activities. While not wishing to be bound by any specific theory or mode of action, the anti cell-proliferative activities of the pharmaceutical composition of the present invention are believed to be attributable to the polysaccharides present in the solution and the biological effect of these polysaccharides is believed to be primarily due to their potent immune stimulating properties.

Immune stimulation occurs as a result of injection of substances which themselves have only weak antigenic effects, but are nevertheless able to induce the body's own defense mechanisms in a non-specific or even specific manner. Among other things, these substances generally influence the proliferation of the immunocompetent cells, but they do not leave behind any memory reaction. This means that the primary targets of the action of the immunostimulating substances are the macrophages and granulocytes, as well as T- and B-lymphocytes. The effect of the immunostimulants may be direct or indirect, e.g., via the complement system or the lymphocytes, via the production of interferon or lysosomal enzymes (e.g., lymphokines, colony stimulating factor and others), as well as via the increase in macrophagocytosis and microphagocytosis.

Certain anionic polysaccharides [46, 47], such as dextran sulphate and pustulan sulphate stimulate cell-mediated T-cell dependent immune responses without stimulating antibody mediated immune responses that are B-cell dependent. On the other hand, unmodified polysaccharides stimulate only B-cells and certain other polysaccharides are known to stimulate both T-cell and B-cell responses under certain conditions. At present, the inventors are not aware of a specific test method to measure the stimulating effect of a given compound. Instead, the stimulating effect is measured in an indirect way.

The polysaccharides present in the present pharmaceutical composition (Table 2 above), namely, PS-I, PS-II, PS-III and PS-IV, have been shown to stimulate the immune system by measuring the effect of these polysaccharides on the function and capability of mononucleated systems as well as the ability to stimulate T- and B-lymphocytes. For example, the polysaccharide PS-I is shown to produce 256 Unit/mL of Tumor Necrosis Factor (TNF) at a concentration of 50 mcg/mL while a mixture of PS-II, PS-III and PS-IV is shown to produce 1000 Unit/mL of TNF at a concentration of 3 mcg/mL. In addition, these polysaccharides have been shown to stimulate the lymphocyte proliferation and phagocyte values as described in the examples below.

While the immune stimulating properties of the polysaccharides present in the substantially sterile extract of the present invention has been established, it is believed that the extract may also contain other molecules both small (i.e., less than 1000 Dalton) and large (i.e., greater than 1000 Dalton) in size with immune stimulating and other biological properties. Thus, the properties of amelioration of the cell-proliferative diseases by the pharmaceutical composition of the present invention is believed not to be limited to the presence of the identified polysaccharides PS-I, PS-II, PS-III and PS-IV in the composition.

Thus, in a preferred embodiment, the present invention provides for the manufacture of a pharmaceutical composition containing NOE powder suitable for paranteral administration to human and animal subjects. In particular, NOE powder and the lyophilized pharmaceutical compositions described in this invention have been shown to be stable up to three years and can be conveniently stored at ambient temperature with minimal or no loss in activity. Furthermore, in a preferred embodiment, the lyophilized vials containing the pharmaceutical composition can be shipped to customers without loosing any biological activities due to ambient temperature and humidity changes. Also, the process of the present invention can be used successfully to scale-up the production of the pharmaceutical composition described here.

Another aspect of the present invention is directed to therapeutically inhibiting cell-proliferative diseases such as cancer and and immune deficient diseases such as AIDS. Accordingly, human patients suspected of having a malignant cell-proliferative disease or viral disease, such as AIDS, are initially given a low daily dose of 0.3 mL of the pharmaceutical composition of NOE of the present invention intramuscularly on the first day and the dosage is increased to 0.5 mL within the next seven days. After seven days, the patients are placed on an initial therapeutic regimen utilizing NOE. This therapeutic regimen is performed typically for once a day for a period of three months to one year depending upon the severity of the disease. Following completion of a normal therapeutic regimen, a patient is then placed on a maintenance therapeutic regimen for a period of time ranging from about six months to about three years. During this period NOE is administered once every two days for a period of about six months. After this treatment, the patient is given NOE once a week for up to three years.

In order to illustrate the anti cell-proliferative and pain remediation activities of the present pharmaceutical formulation we have provided five case reports in Examples 8–16 below of human subjects who have been treated with the pharmaceutical composition of the present invention.

The pharmaceutical composition according to the present invention offers several advantages over the formulations disclosed in U.S. Pat. No. 5,135,745 [Ozel, 20]. Specifically, Ozel teaches a screening technique in which potential patients are assessed for the onset of fever as the benchmark for treatment. In other words, Ozel teaches that only those patients who develop an initial fever are suitable for receiving a therapeutic regimen of the formulation. In contrast, the present inventors have surprisingly and unexpectedly discovered that the onset of fever is not necessarily linked to efficacy of the present substantially sterile extract of Nerium species. Specifically, after taking the present formulations intramuscularly the patients do not produce fever as in the case of the previous formulation. Thus, whereas the original Ozel formulation teaches awaing from efficacy in patients who do not exhibit the onset of fever, the present pharmaceutical composition is effective, regardless of whether fever occurs in the patient. This renders the present pharmaceutical compositions useful in a wide variety of patients and in a more patient-friendly manner. Further, the present substantially sterile extract of Nerium species is stable for several years unlike the original crude extract of Ozel [20].

A number of excipients may be appropriate for use in the formulations, which comprise the composition according to the present invention. The inclusion of excipients and the optimization of their concentrations for their characteristics will be understood by those ordinarily skilled in the art.

Embodiments of the invention will now be illustrated with reference to the following Examples. The Examples are intended to be merely illustrative of the invention and should not be used to limit or construe the invention.

EXAMPLE 1

Preparation of Freeze-Dried *Nerium Oleander* Extract (NOE) Powder

Branches of *Nerium Oleander* plant grown under quarantine conditions were washed thoroughly two times with tap water, one time each with deionized (DI) water and sterile Type I water (Nanopure UV Ultrapure Water System, Barnstead) and then cut into pieces of about one inch. The cut stems and leaves were weighed and transferred into a 50 L glass round bottom flask, which was placed onto a mantle.

To approximately 7 kg of leaves and stems, 30 L of sterile Type I water was added to the flask. A ground joint with a condenser and a thermometer was then attached to the flask, and it was heated for 4 hours after the mixture started boiling. The boiled oleander extract was cooled then to between 60° and 70° C. The solution was transferred, employing a peristaltic pump, into a sterile Corning 0.22 μm cellulose acetate bottle-top filter with a glass-fiber pre-filter, attached to a sterile 2 L media bottle (Corning) in a laminar flow hood (LABGRAD). A diaphragm pump (Gast) was connected to the bottle-top filter to filter-sterilize the solution into the media bottle. Immediately after filtering about 2 L of the solution, the bottle-top filter was removed from the media bottle and the bottle was closed tightly with a cap, inside the hood. Thirteen such 2L bottles with about 26.5L of the filter-sterilized solution were heated to about 100° C. for 1 hour by placing these bottles in a water-bath pre-heated to 100° C. These media bottles with the hot sterile solution were cooled to room temperature, and then stored at 4° C. in a refrigerator. The sterile extract stored at 4° C. in the media bottles was stable for more than 6 months.

Two liters per tray of the above-refrigerated solution was transferred from the media bottle into a sterile stainless steel tray. This tray was then covered with a stainless steel lid with an opening for thermocouple. Three such trays containing about 6 L of solution was placed onto three stoppering trays of a Labconco™ Freeze-Dryer pre-cooled to −40° C. A thermocouple was introduced into the solution in each one of the trays through the slot in the stainless steel tray lid, and the extract was cooled to −40° C. in 8 hours. The sample frozen to −40° C. was evacuated for 3 hours using a vacuum pump. The temperature of the stoppering trays was raised to 10° C. and the sample was evacuated for 4 days. Then the temperature of the stoppering trays was further raised to 30° C. and evacuated at this temperature for 2 days allowing the freeze-dried powder to attain the stoppering tray temperature. The vacuum pump was then turned off and the vacuum in the stoppering tray compartment was released. Then the stainless steel trays with the freeze-dried powder were removed from the freeze-dryer. The freeze-dried powder was immediately transferred into a pre-weighed clean and sterile plastic container. Six liters of the extract yielded about 95 g of the freeze-dried powder. The freeze-dried powder was stored at −20° C. in a freezer for further use. It is believed that the oleander extract in the freeze-dried powder form is stable at least for about 3 to 5 years.

EXAMPLE 2A

Formulation with 1.5% Freeze-Dried *Nerium Oleander* Extract (NOE) Powder and 5% Mannitol A formulation comprising 1.5% of the freeze-dried oleander powder from Example 1, 5% mannitol as bulking agent, 0.5% sodium ascorbate and 0.02% ascorbic acid as antioxidants, 0.1% methylparaben sodium and 0.01% propylparaben sodium as preservatives and Sterile Type I water (see Table 3) was prepared under aseptic conditions following the method given below.

TABLE 3

| Ingredient | w/v (%) | Amount (g) |
| --- | --- | --- |
| NOE Powder (from Example 1) | 1.5 | 30.0 |
| Mannitol | 5.0 | 100.0 |
| Sodium Ascorbate | 0.5 | 10.0 |

TABLE 3-continued

| Ingredient | w/v (%) | Amount (g) |
| --- | --- | --- |
| Ascorbic Acid | 0.02 | 0.4 |
| Methylparaben Sodium | 0.1 | 2.0 |
| Propylparaben Sodium | 0.01 | 0.2 |
| Sterile Type I Water | Qs to 2000 mL | |

The ingredients mannitol, sodium ascorbate, ascorbic acid, methylparaben sodium, propylparaben sodium were purchased as USP grade materials from Spectrum Chemical and Safety Products.

A 2000 mL graduated glass cylinder was weighed and tarred, and the ingredients listed in Table 3 were weighed and transferred directly into the glass cylinder. A magnetic stirrer bar was placed inside the glass cylinder, which was placed over a Thermolyne stir plate. Type I water was added and the volume was adjusted to 2000 mL. The ingredients were stirred for about 5 minutes to form a clear solution. The pH of the solution measured using a Beckman Φ200 pH meter was approximately 6.49. When required, the pH of the solution was adjusted using either 1N NaOH or 1N HCl to 6.5±0.2. The solution was transferred into a sterile 2L media bottle, capped and heated to 70° C. in a pre-heated circulating water-bath. The hot solution was filtered using a 0.22 μm sterile cellulose acetate bottle-top filter with a glass pre-filter attached to a sterile media receiver bottle in the laminar flow hood. A diaphragm pump (Gast) was connected to the bottle-top filter to filter-sterilize the solution into the media bottle. Immediately after filtering the solution, the bottle-top filter was removed and a bottle-top dispenser (Dispensette II, Brinkmann) was attached to fill 10 mL of the sterile liquid at a time in 10 mL sterile glass vials in the laminar flow hood. To each one of the 10 mL vials filled with the NOE formulation, a 3-leg gray butyl rubber stopper (Wheaton) was placed in such a way that the stopper openings were exposed outside the mouth of the vial. About 188 of these vials were arranged in two sterile stainless steel trays, and these trays were then placed onto the freeze-dryer stoppering trays pre-cooled to −40° C. After 7 hours, the sample was freeze-dried using following the following temperature cycle:

−35° C. for 6 hours;

0° C. for 72 hours; and

30° C. for 24 hours.

The vials with freeze-dried NOE were stoppered under a vacuum level of about $38 \times 10^{-3}$ Mbar in the stoppering tray. The vacuum pump was turned off, vacuum in the stoppering tray compartment was released, and the stainless steel trays with the vials were removed from the freeze-dryer. Each one of the vials was sealed with a flip-cap aluminum seal (Wheaton) employing a hand operated E-Z crimper. The pharmaceutically formulated freeze-dried NOE composition, when stored at room temperature in the vacuum sealed vials is stable at least for about 3 to 5 years.

EXAMPLE 2B

Reconstitution of NOE Formulation

The reconstitution of the formulated NOE freeze-dried composition in the vacuum sealed vials made in accordance with Example 2A was performed following the procedure given below:

10 mL of sterile water for injection was withdrawn using a sterile 10 mL syringe with a 20 G×1" needle attached to it.

The flip-cap was detached from the aluminum seal in the vial, and the exposed surface of the rubber stopper was cleaned with 70% isopropanol.

The water for injection from the syringe was dispensed into the vial. Because the powder in the vial was under vacuum, as soon as the syringe needle was inserted, the vacuum automatically withdrew the water into the vial without having to use the syringe plunger.

After adding the water for injection, the powder was reconstituted into a clear solution within a minute. The reconstituted NOE solution was used for the case studies reported in Examples 8–12 hereinbelow.

EXAMPLE 2C

Stability of Reconstituted NOE Formulation

The testing was performed by storing the vials containing the reconstituted solution at 4° C. and room temperatures. The formulated NOE solution was stable for at least one month when stored at these temperatures. There was no visible precipitation of molecules in the solution appear to inhibit the precipitation of high molecular weight polysaccharide molecules in the NOE formulation.

EXAMPLE 2D

Sterility of Reconstituted NOE Formulation

The freeze-dried formulated NOE composition was reconstituted with 10 mL sterile water for injection in a laminar flow hood under aseptic conditions at the Southwest Bioscience Laboratories, San Antonio and tested in accordance with the procedure recommended by US Pharmacopeia XXIII. The formulated NOE solution was inoculated in a culture bottle (BBL Septi-Check) containing either 70 mL Casein Digest Broth with SPS and $CO_2$ or Thioglycollate Broth with SPS and $CO_2$. The Casein Digest Broth was aerated using a 0.2 μm filter for aerobic growth. The Casein Digest and Thioglycollate Broths were incubated at 2520 C. and 5° C. for 7 days, respectively. These samples were examined each day for growth and retained for 14 days before discarding. For 14 days the cultures were also observed for microbial growth after incubating under the same conditions as the samples. No microbial growth was observed in the cultures with or without formulated NOE solution, indicating that the freeze-dried formulated NOE powder was sterile.

EXAMPLE 3

Formulation with 1.5% Freeze-Dried *Nerium Oleander* Extract (NOE) Powder and 2% Mannitol A formulation with 1.5% of the freeze-dried oleander powder from Example 1, 2% mannitol as bulking agent, 0.5% sodium ascorbate and 0.02% ascorbic acid as antioxidants, 0.1% methylparaben sodium and 0.01% propylparaben sodium as preservatives (Table 4) was prepared under aseptic conditions following the method given in Example 2A. A 2000 mL glass cylinder was weighed and tarred, and the following ingredients (Table 4) except water were weighed and added directly into the glass cylinder. Type I water was added to the mixture and the volume of the mixture was adjusted to 2000 mL.

TABLE 4

| Ingredient | w/v (%) | Amount (g) |
|---|---|---|
| NOE Powder (from Example 1) | 1.5 | 30.0 |
| Mannitol | 2.0 | 20.0 |
| Sodium Ascorbate | 0.5 | 10.0 |
| Ascorbic Acid | 0.02 | 0.4 |
| Methylparaben Sodium | 0.1 | 2.0 |
| Propylparaben Sodium | 0.01 | 0.2 |
| Sterile Type I Water | Qs to 2000 mL | |

The pH of the solution was maintained at approximately 6.49. The freeze-dried NOE powder in 10 mL vials with the ingredients in Table 4 was reconstituted with 10 mL sterile water forming a clear solution within a minute.

EXAMPLE 4

Formulation with 1.5% Freeze-Dried NOE Powder without Mannitol

A formulation with 1.5% of the freeze-dried NOE powder from Example 1, 0.05% sodium ascorbate and 0.02% ascorbic acid as antioxidants, 0.1% methylparaben sodium and 0.01% propylparaben sodium as preservatives (Table 5) was prepared under aseptic conditions following the method given in Example 2A. A 2000 mL glass cylinder was weighed and tarred, and the following ingredients (Table 5) except water were weighed and added directly into the glass cylinder. Type I water was added to the mixture and the volume of the mixture was adjusted to 1000 mL. The pH of the solution was approximately 6.49. The freeze-dried powder in 10 mL vials with the ingredients in Table 5 was reconstituted with 10 mL sterile water forming a clear solution within a minute.

TABLE 5

| Ingredient | w/v (%) | Amount (g) |
|---|---|---|
| NOE Powder (from Example 1) | 1.5 | 15.0 |
| Sodium Ascorbate | 0.5 | 5.0 |
| Ascorbic Acid | 0.02 | 0.2 |
| Methylparaben Sodium | 0.1 | 1.0 |
| Propylparaben Sodium | 0.01 | 0.1 |
| Sterile Type I Water | Qs to 1000 mL | |

EXAMPLE 5

Formulation with 1.5% Freeze-Dried NOE Powder, 5% Mannitol and 0.2% Solubilizer

A formulation with 1.5% of the freeze-dried oleander powder from Example 1, 5% mannitol as a bulking agent, 0.2% Tween 80 or Tween 20 as a solubilizer/surfactant, 0.5% sodium ascorbate and 0.02% ascorbic acid as antioxidants, 0.1% methylparaben sodium and 0.01% propylparaben sodium as preservatives (Table 6) was prepared under aseptic conditions following the method given in Example 2A. A 500 mL glass cylinder was weighed and tarred, and the following ingredients (Table 6) except water were weighed and added directly into the glass cylinder. Type I water was added to the mixture and the volume of the mixture was adjusted to 500 mL.

TABLE 6

| Ingredient | w/v (%) | Amount (g) |
|---|---|---|
| NOE Powder (from Example 1) | 1.5 | 4.5 |
| Mannitol | 5.0 | 20.0 |
| Sodium Ascorbate | 0.5 | 1.5 |
| Ascorbic Acid | 0.02 | 0.06 |
| Solubilizer* | 0.2 | 0.6 |
| Methylparaben Sodium | 0.1 | 0.3 |
| Propylparaben Sodium | 0.01 | 0.2 |
| Sterile Type I Water | Qs to 300 mL | |

*Tween 80 ™ or Tween ™ 20

The pH of the solution was maintained at approximately 6.52. The freeze-dried NOE powder in 10 mL vials with the ingredients in Table 6 was prepared as described in Example 2A. The powder was reconstituted with 10 mL sterile water forming a clear solution within a minute.

EXAMPLE 6

Formulation with 1.5% Freeze-Dried NOE Powder, 5% Sugar

A formulation with 1.5% of the freeze-dried oleander powder from Example 1, 5% Sugar (glucose or fructose or dextrose or lactose) as a bulking agent, 0.5% sodium ascorbate and 0.02% ascorbic acid as antioxidants, 0.1% methylparaben sodium and 0.01% propylparaben sodium as preservatives (Table 7) was prepared under aseptic conditions following the method given in Example 2A. A 500 mL glass cylinder was weighed and tarred, and the following ingredients (Table 7) except water were weighed and added directly into the glass cylinder. Type I water was added to the mixture and the volume of the mixture was adjusted to 300 mL.

TABLE 7

| Ingredient | w/v (%) | Amount (g) |
|---|---|---|
| NOE Powder (from Example 1) | 1.5 | 4.5 |
| Sugar* | 5.0 | 20.0 |
| Sodium Ascorbate | 0.5 | 1.5 |
| Ascorbic Acid | 0.02 | 0.06 |
| Methylparaben Sodium | 0.1 | 0.3 |
| Propylparaben Sodium | 0.01 | 0.2 |
| Sterile Type I Water | Qs to 300 mL | |

*Sugar was glucose or fructose or dextrose or lactose monohydrate

The pH of the solution with glucose, fructose, dextrose and lactose monohydrate was approximately 6.51, 6.48, 6.42 and 6.59, respectively. The freeze-dried NOE powders in 10 mL vials with the ingredients in Table 7 were prepared as described in Example 2A. The powders were reconstituted with 10 mL sterile water forming clear solutions within a minute.

EXAMPLE 7

Oleander Cream with 2% Oleander Extract

The lipophilic agents and emulsifiers (Phase A) as shown below were weighed in a 2 L glass container. A magnetic stirrer bar was placed inside the container with Phase A. The container was placed on a heater with stirrer and the mixture was heated 60° C. to 70° C. and stirred in order to accelerate the dissolution process and to form a clear oil phase. The aqueous Phase B, as shown below with the oleander extract, emulsifier and other hydrophilic agents with water were weighed in a 3 L stainless steel container. The mixture was heated 60 to 70° C. and stirred with a stainless steel spoon to form a clear solution. The cream was prepared by adding the oil Phase A to the aqueous Phase B under mixing with a mixer (ChefMix™, 275 Watts, Hamilton Beach).

| Phase A | |
|---|---|
| Meezawax | 100.0 g |
| Glycerylmonostearate | 100.0 g |
| Cetyl Alcohol | 110.0 g |
| Petrolatum0 | 50.0 g |
| Polyoxyl 50 Stearate | 150.0 g |
| Lanolin alcohol | 50.0 g |
| Liquid Lanolin | 50.0 g |
| Vitamin E Acetate | 25.0 g |
| Methylparaben | 2.5 g |
| Propylparaben | 0.25 g |
| Fragrance | 25.0 g |
| Phase B | |
| Potassium Sorbate | 2.5 g |
| Tween ™ 20 | 125.0 g |
| Oleander Extract | 50.0 g |
| Glycerol | 250.0 g |
| Water qs to | 2500.0 g |

In the following Examples, the patients were given the NOE formulation of Example 2A by intramuscular injections and the protocol for the dosage is given in Table 8. In addition, the patients were given the NOE formulation of Example 7 by topical applications. As can be seen from these Examples, the pharmaceutical composition of the present invention has ameliorated the sufferings of these patients from the cell-proliferative diseases.

TABLE 8

Dosage for Treating Cancer and AIDS in humans

1. Initial Therapeutic Regimen
Daily Intramuscular injections with 25 gauge needle on the following protocol:

| | |
|---|---|
| Day # 1–3 | 0.3 mL |
| Day # 4–6 | 0.4 mL |
| Day # 7 to completion | 0.5 mL |

2. Maintenance Therapeutic Regimen
Intramuscular injections with 25 gauge needle on the following protocol:

| | |
|---|---|
| One injection every two days for six months | 0.5 mL |
| One injection every seven days up to three years | 0.5 mL |

EXAMPLE 8

Case Report: Prostate Cancer with Bone Metastasis

A white male patient, born on Jan. 26, 1943, was diagnosed with carcinoma of the prostate gland. A bone scan carried out approximately two years later showed that a focal area of increased isotope uptake on the delayed bony images in the left side of L2 vertebral body and also to the posterior spinal process of T12-vertebrae. Saggital views confirmed the isotope uptake was in the spinous process, and not in the body of the vertebrae. A very small focal area of increased isotope uptake was identified in the mid left superior pubic ramus. At the time the patient was suffering from severe back pain, appeared sick with low energy level, and looked pallor.

The patient started the following NOE treatment shortly after the bone scan. A daily dose of 0.5 mL NOE solution, prepared according to the procedure described in Example 2, was administered intramuscularly. Following the NOE treatment, the patient was examined approximately one month later. At the time the patient was pain-free (this exemplifies the pain remission advantage of the present pharmaceutical composition) and appeared well with good color and high energy. His Prostate Specific Antigen (PSA) concentration was reduced from 8.9 at the beginning of treatment to 0.5 indicating a significant reduction or remission of prostate cancer. The patient continued the NOE treatment schedule. A bone scan was again performed approximately four months after the beginning of treatment. Comparison of the pre-treatment and post-treatment bone scans indicated a significant reduction in the isotope uptakes in the posterior spinal process of T12 and in the left side of the L2 vertebral body following the NOE treatment. This indicates a favorable response from the NOE therapy. However, the minor focal increased isotope uptake in the left superior pubic ramus was relatively unchanged. But there was no progression of the disease at this site. The patient has been continued with the daily injection dose of 0.5 mL NOE.

EXAMPLE 9

Case Report: Breast Cancer

A white female patient born on Dec. 8, 1942 was diagnosed with carcinoma in her right breast about fifteen years ago. Eventually, she had a mastectomy for severely advanced cancer in her breast. However, initially she refused conventional surgery and decided to start with an alternative non-conventional therapy to fight her cancer.

She received treatments, including detoxification and strict diet control. These treatments also included high doses of Vitamin B12 and Vitamin C as food supplement. Although these treatments reduced her breast cancer growth, she developed other complications such as metastases in lumbar spine, sacrum, scapula, rib cage, femur and pleurae mediastinum. The patient was therefore admitted into a hospital for further evaluation. Because her tumors were estrogen sensitive, she was advised to take Tamoxifen™. As she could not tolerate the side effects of Tamoxifen™, she discontinued taking the drug after two weeks. While she was taking Tamoxifen™ there appeared to be some improvements in her condition. However, her condition deteriorated gradually after discontinuing the drug.

She was admitted to a hospital approximately one year later on three separate occasions with severe pain in the lumbar spine due to collapse of lumbar vertebrae. She was also admitted with severe dyspneoa on three occasions due to large pleural effusion, which required aspiration and drainage. This procedure was carried out on three occasions, and each time approximately 700 mL of pleural fluid was drained. Subsequently, she experienced considerable weight loss, severe back pain, extreme weakness and breathlessness. Her hemoglobin (Hb) dropped to less than 10 g/dL. Her Erythrocyte Sedimentation Rate (ESR) reached 129 mm/hr and her Breast C Antigen CA15-3 was 582.0 U/mL. The X-ray taken in approximately 18 months ago showed a large pleural effusion on the left side and this was not aspirated. The patient was declared terminally ill and her life expectancy was estimated to be about three months.

The patient started receiving NOE treatment at the time of her terminal illness prognosis. Initially, she was administered 0.3 mL of NOE by intramuscular injection as prepared in accordance with Example 2A. The dosage was then increased to 0.5 mL and eventually to 0.6 mL daily. Initially she experienced pain in her bone, however, within two weeks following the NOE treatment she felt an overall improvement in her condition. She started breathing well, her energy levels increased and her pain levels dropped (i.e., pain remission).

Following NOE treatment for two months, her medical condition improved dramatically. A X-ray taken approximately three months after the initial X-ray showed a major reduction of the left pleural effusion, sclerosis in right scapula and ribs. Full blood haematology results indicated an increase in hemoglobin count from 10 to 14 g/dL, and that the ESR dropped dramatically from 129 mm/hr to 4 mm/hr. Her Breast C Antigen CA15-3 was down from 582.0 U/mL to approximately 200 U/mL. She gained approximately 18 lb in weight.

A CT scan performed approximately eight months after the beginning of treatment demonstrated that the pleural and pulmonary nodules had almost completely disappeared. It also revealed regression of the fullness in the left hilar region and healing sclerosis of previous right lower scapular metastases. The posterior right pleural thickening was found to have significantly improved. No bony destructive lesion was appreciated. The patient was recommended to continue NOE treatment with daily injections.

EXAMPLE 10

Case Report: Prostate Cancer

A white male patient born on Jul. 6, 1926 was examined in a hospital and swelling of his right sternoclavical joint was noted. He also appeared pale and looked unwell. All primary investigations including haemoglycogical check-up and total haemological screen X-rays as well as plain x-rays revealed no pathological sign. He was later referred for a bone scan, which was also negative. The only abnormality was that his PSA was raised to 4.7. Physical examination could not reveal any other abnormality and his blood test results were within normal limits. No tumor was detected in his prostate gland. He was admitted to a hospital for a more detailed medical examination. No carcinoma was detected at this institution. The patient was advised not to take any medication and return for review in six months time to recheck his PSA.

Subsequently, the patient's PSA increased to 20, and he was again admitted to Limerick Regional hospital for another detailed medical examination. Ultrasound of the prostate gland showed a large hyperemic area. Biopsy results indicated carcinoma of the prostate following hisptopathological examination of the specimen. It was decided to commence him on monthly long acting LIIRG Analogue injection. He started his first treatment of Prostrap SR and Flutimide for one month approximately eighteen months ago.

The patient started a daily injection of 0.5 mL of the NOE composition made in accordance with Example 2A approximately eighteen months ago and his medical condition improved gradually. The PSA concentration dropped from 20 to 0.5 in four months. The patient continued to have the NOE treatment, however, he had one monthly injection of Leuprorclin acetate for three months. Thereafter the patient discontinued the Leuprorclin acetate injection, but continued with NOE treatment of 0.4 mL/3 times per week. During this period, his blood tests remained within normal limits. There was no evidence that the NOE treatment caused him any adverse reactions. His PSA concentration measured approximately eight months ago was 0.7, an extremely low level.

His Blood Counts, Liver Function Tests, Urinalysis, Uica and Electrolytes remained normal. As of current date, the patient has no signs of cancer He is continuing twice weekly injection for another three months.

EXAMPLE 11

Case Report: AIDS with Hepatitis C

A white female patient born on Jun. 15, 1968 was first diagnosed approximately seven years ago as being HIV positive and her T-cell count was 300. She was also diagnosed with Hepatitis C. She contracted the HIV from her husband, and the Hepatitis C from a blood transfusion service. The patient was admitted to a Hospice almost two years ago. She was very fatigued, the liver was enlarged, thrush was apparent around her vagina in addition to having warts on the back of both hands.

The patient started the NOE treatment on approximately two years ago. The initial dosage of the NOE composition made in accordance with Example 2A injected intramuscularly was 0.3 mL/day, 6 days a week. The dosage was gradually increased to 0.5 mL/day within a week and maintained at this level. A blood test performed approximately three months after beginning treatment demonstrated no sign of hepatic illness. However, the liver function tests indicated permanent liver damage and T-cell count was increased to 630.

The patient was clinically examined approximately 3½ months at Milford Hospice. She was found to be in excellent medical condition. The energy level was on the same level of a healthy person. The thrush disappeared, the warts were no longer apparent and there was no obvious swelling of the liver.

The patient continued daily NOE injections for approximately one year and was then started on a maintenance regimen with two NOE injections per week. The patient was again examined on approximately nine months after the beginning of treatment and her T cell count was further increased to 880. The patient continues with the maintenance NOE treatment. During the NOE treatment, she receives no adjuvant therapy.

EXAMPLE 12

Case Report: Cholangiocarcinoma

A white female patient born in Jan. 25, 1962 experienced abdominal pain and weight loss. Obstructive jaundice then occurred. ERCP (endoscopic retrograde cholangiopancreatography) and CAT scan were performed a revealed a significant stricture of the common right and left hepatic ducts. A stent was implanted and the patient underwent surgery and was found to have a small cicatrising mass at the hilum which involved the port vein posterially with adjacent metastatic lymph nodes. Biopsies confirmed the presence of an infiltrating carcinoma consistent with primary carcinoma of the bile duct. A segment III bypass was then performed. The patient's jaundice settled but the patient was discharged from the hospital when it was determined that chemotheraphy and/or radiotheraphy were not likely to be of any benefit to her.

By the time that the patient presented to a hospice (approximately 3 months after onset of the original symptoms), she had lost approximately 42 pounds and was in very poor medical condition. The patient started NOE treatment in an initial regimen comprising a daily I.M. injection dosage of 0.3 cc which was increased to 0.5 cc after one week and maintained.

The patient's general medical condition improved gradually. After approximately 3 months of treatment, the patient had gained approximately 28 pounds in weight and a follow-up CAT scan revealed no tumoral mass. An ERCP was performed approximately two months later to remove the stent. The ERCP also confirmed the absence of a tumoral mass.

The patient was then placed on a maintenance regimen comprising sublingual adminstration of NOE extract 3×0.3 cc every day.

EXAMPLE 13

Case Report: Solar Keratosis

A male patient born on Mar. 1, 1920 presented with an area of solar keratosis with thickening. The patient started the topical treatment of a cream with NOE powder prepared according to the procedure described in Example 7. Six weeks after he commenced on topical application of the cream twice daily, the healing was phenomenal. The attending physician, a specialist in palliative care, was able to remove all dead tissue and underneath there was normal skin.

EXAMPLE 14

Case Report: Solar Keratosis

A male patient born on Mar. 9, 1938 suffered with severe solar keratosis covering most of his forehead on his high receding hairline and onto his scalp. Both his ears were also affected by this condition. He was prescribed cream with NOE powder prepared according to the procedure described in Example 7. Just after five months of topical application of the cream twice daily he is now free of keratosis.

EXAMPLE 15

Case Report: Skin Carcinoma

A male patient born on Jul. 6, 1926 presented with severe history of carcinoma of skin and lower lip. In the past he had undergone radiotherapy for squamous cell carcinoma. He had radiotherapy to his lip and to the left pre-auriclar area. Subsequently, he presented with severe solar keratosis on his forehead, both ear lobes, auricle and his maxillary and mandibular areas. After two months of topical application (twice daily) of cream with NOE powder prepared according to the procedure described in Example 7 he made an excellent recovery and is now free from all solar keratosis.

EXAMPLE 16

Case Report: Squamous Cell Carcinoma

A 92 year old woman was presented with severe advanced squamous cell carcinoma of her right lower leg and calf. She had five lesions both posterior and anterior aspects of her right tibial area. Some of these lesions were quite deep and measured two inches by one and half inches in circumference. They had very sluffy interiors. She was treated twice daily with topical cream with NOE powder prepared according to the procedure described in Example 7 on those lesions for a period on nine months.

The condition was halted in its progress by this treatment which was applied daily. She showed evidence of healing at the edges of the lesions but her condition was quite severe. Although there was still evidence of healing process from the treatment she received, the patient died from septicaemia from cellutitis she developed from the other leg which was free from cancer and had also developed bronchial pneumonia.

However, it is important to note that she had a positive response to the cream on her lesions and she required very little analgesia and certainly had no deterioration in her condition over the last nine months of her life.

EXAMPLE 17

Case Report: Peritoneal Carcinoma

A 57 year old female patient present with severe abdominal pain and was admitted to a hospice. The patient had previously been diagnosed as having carcinoid syndrome with metastases in her peritoneum. Clinical examination revealed a palpable tumor at the suprapubic site. The patient had chronic diarrhea and vomiting symptoms. She was using morphine and analgesics to control her pain. Following palliative medication, she was discharged from the hospice approximately 1 month after being admitted.

The patient then started to receive an intramuscular injection of NOE extract. The initial daily dosage was 0.3 cc which was increased over the first week of treatment to 0.5 cc and maintained at this level.

The patient's general medical condition improved gradually and her energy level increased. At an examination conducted approximately 2½ months, the peritoneal tumer were palpated to have decreased in size. A CAT scan performed at that time corroborated the size reduction of the tumors. The patient was using reduced amounts of morphine and analgesic.

A follow-up CAT scan performed approximately 5 months after the onset of treatment with the NOE extract revealed no tumor in the peritoneum. The patient has been gradually withdrawing from the use of morphine.

EXAMPLE 18

Case Report: Prostate Cancer

A 73 year old male patient presented feeling unwell and had been suffering with recurring infections in his chest over the past six weeks. He had loss of energy, was sweating profusely at night and was feeling very weak. The patient had a history of benign prostate hypertrophy for which he previously had surgery.

The patient had a series of blood test which revealed that all conventional blood parameters were within normal limits with the exception of PSA which was 13.8 (normal value is less than 4). High values of PSA are normally indicative of carcinoma of the prostate.

The patient then started to receive an intramuscular injection of NOE extract. The initial daily dosage was 0.3 cc which was increased over the first week of treatment to 0.5 cc and maintained at this level. After approximately 1½ months of treatment, the patient's blood PSA level was 8.1. After approximately 4 months of treatment, the patient's blood PSA level was 5.4. After approximately 5 months of treatment, the patient's blood PSA level was 0.9.

REFERENCES

The following documents are referred to in this specification and the contents of each reference is hereby incorporated by reference:
1. Dymock W., *Pharmacographia Indica*, 2, 398, (1890).
2. Chopra R. N., Nayar S. L. and Chopra I. C., *Glossary of Indian Medicinal Plants*, CSIR, New Delhi (1956), page 175.
3. Dey K. L. and Bahadur R., *Indigenous Drugs of India*, International Book Publishers, India (1984).
4. Kirtikar K. R. and Basu B. D., *Indian Medicinal Plants*, International Book Ditributors, India (1987).
5. Krasso et al., *Helv. Chim. Acta*, 46, 1691 (1963).
6. Taylor A., McKenna G. F. and Burlage H. M., *Texas Reports on Biology and Medicine*, 14, 538 (1956).
7. Siddiqui S., Hafeez F., Begum S. and Siddiqui B. S., *J. Nat. Products*, 49, 1086 (1987).
8. Siddiqui S., Siddiqui B. S., Hafeez F. and Begum S., *Planta Med.*, 53, 424 (1987).
9. Siddiqui S., Siddiqui B. S., Hafeez F. and Begum S., *Planta Med.*, 54, 232 (1988).
10. Siddiqui S., Hafeez F., Begum S. and Siddiqui B. S., *J. Nat. Products*, 51, 229 (1988).
11. Siddiqui B. S., Begum S., Hafeez F. and Siddiqui S., *Phytochemistry*, 28, 1187 (1995).
12. Siddiqui S., Hafeez F., Begum S., and Siddiqui B. S., *Phytochemistry*, 26, 237 (1987).
13. Siddiqui B. S., Begum S., Siddiqui S. and Lichter W., *Phytochemistry*, 39, 171 (1995).
14. Abe F. and Yamauchi T., *Phytochemistry*, 31, 2459 (1992).
15. Hanada R., Abe F. and Yamauchi T., *Phytochemistry*, 31, 3183 (1992).
16. Hanada R., Abe F. and Yamauchi T., *Phytochemistry*, 31, 2459 (1992).
17. Siddiqui S., Begum S., Siddiqui B. S. and Hafeez F., *J. Nat. Products*, 52, 229 (1988).
18. Siddiqui S., Siddiqui B. S., Begum S., and Hafeez F., *Plant Med.*, 55, 292 (1989).
19. Siddiqui S., Begum S., Hafeez F. and Siddiqui B. S., *Phytochemistry*, 28, 1187 (1989).
20. Huseyin Z. Ozel, U.S. Pat. No. , 5,135,745.
21. Huseyin Z. Ozel, Private Communications.
22. Canadian patent application 2,016,948 naming as inventors Ozel H. Z., Baser K. H. C., Carbik, I. and Wagner H.
23. Xu H., Zeng F., Wan M. and Sim K., *J. Nat. Products*, 59, 643 (1996).
24. Chihara G., *Farumashia Rev.*, 6, 119 (1981).
25. Suzuki I., Itani T., Ohno N., Oikawa S., Sato K., Miyazaki T. and Yadomae T., *J. Pharmcobio. Dyn.*, 8, 217 (1985).
26. Ohno N., Iino K., Oikawa S., Sato K., Ohsawa M. and Yadomae T., *Chem. Pharm. Bull.*, 34, 3328 (1986).
27. Taguchi T., *Jpn. J. Cancer Chemotherapy*, 10, 387 (1983).
28. Kosaka A., Imaizumi A., Hattori Y, Mori F., Wani T. and Yamashita A., *Jpn. J. Cancer Chemotherapy*, 11, 1399 (1984).
29. Wagner H., Proksch A., Riess-Maurer J., Vollner A., Odenthal S., Stuppner H., Jurcic K., Le Turdu M. and Fang J. N., *Arzneiz. Forsch.*, 35, 1069 (1985).
30. Fang J. N., Proksch A. and Wagner H., *Phytochemistry*, 24, 2619 (1985).
31. Kumazawa Y, Mizunoe K. and Otsuka Y, *Immunology*, 47, 75 (1982).
32. McCarthy R. E., Arnold L. W. and Babcock G. F., *Immunology*, 32, 964 (1977).
33. Mizumoto K., Sugawara I., Ito W., Kodama T., Hayami M. and Mori S., *Jpn. J. Exp. Med.*, 58, 145 (1988).
34. Hamuro J., Hadding U. and Suermann B. D., *Immunology*, 34, 695 (1978).
35. Yamada H., Kiyohara H., Cyong J. C. and Otsuka Y, *Mol. Immunology*, 22, 295 (1985).

36. Yamada H., Ohtani K., Kiyohara H., Cyong J. C., Otsuka Y., Ueno Y. and Omura S., *Planta Med.*, 2, 121 (1985).
37. Tomoda M., Yokoi M. and Ishikawa K., *Chem. Pharm. Bull.*, 29, 2877 (1981).
38. Wagner H., Flachsbarth H. and Vogel G., *Planta Med.*, 41, 252 (1981).
39. Kiho T., Sakai M., Ukai S., Hara C. and Tanaka Y., *Carbohydrate Res.*, 142, 344 (1985).
40. Tubaro A., Tragni E., Del Negro P., Galli C. L. and Della Loggia R., *J. Pharm. Pharmacol.*, 39, 567 (1987).
41. Hikino H., Konno C., Mirin Y and Hayashi T., *Planta Med.*, 4, 339 (1985).
42. Hikino H., Takahashi M., Otake K. and Konno C., *J. Nat. Products.*, 49, 293 (1986).
43. Konno C. and Hikino H., *Int. J. Crude Drug Res.*, 25, 53 (1987).
44. Yamamoto N., Nakashima H., Yoshida O., Kaneko Y, Matsuzaki K. and Uryu T., *Arch. AIDS Res.*, 1, 45 (1987).
45. Yoshida O., Nakashima H., Yoshida T., Kaneko Y., Yamamoto I., Matsuzaki K., Uryu T. and Yamamoto N., *Biochem. Pharmacol.*, 37, 2887 (1988).
46. Baba et al., *Proc. Nat. Acad. Sci., USA*, 85, 6132 (1988).
47. Baba et al., *Antiviral Res.*, 9, 335 (1988).
48. Blattner W. A. in *Viral Infections of Humans*, ed., Evans A. S., Plenum Publishing Co., New York (1991), page 545.

What is claimed is:

1. A substantially sterile water-extract of Nerium species having an endotoxin concentration of less than about 150 units/mL.
2. The extract defined in claim 1, wherein the Nerium species comprises *Nerium oleander*.
3. The extract defined in claim 1, wherein concentration of endotoxins in the extract is in the range of from about 20 units/mL to about 150 units/mL.
4. The extract defined in claim 1, wherein concentration of endotoxins in the extract is in the range of from about 20 units/mL to about 120 units/mL.
5. The extract defined in claim 1, wherein concentration of endotoxins in the extract is in the range of from about 20 units/mL to about 100 units/mL.
6. The extract defined in claim 1, wherein concentration of endotoxins in the extract is in the range of from about 20 units/mL to about 80 units/mL.
7. The extract defined in claim 1, wherein concentration of endotoxins in the extract is in the range of from about 20 units/mL to about 50 units/mL.
8. The extract defined in claim 1, wherein the extract is in liquid form.
9. The extract defined in claim 1, wherein the extract is in aqueous form.
10. The extract defined in claim 1, wherein the extract is in solid form.
11. The extract defined in claim 1, wherein the extract is in powdered form.
12. The extract defined in claim 11, wherein the powdered form of the extract is prepared by drying a liquid comprising the extract.
13. The extract defined in claim 12, wherein said drying comprises freeze-drying.
14. The extract defined in claim 12, wherein said drying comprises spray-drying.
15. The extract defined in claim 12, wherein said drying comprises at least one of heating and evaporating.
16. A pharmaceutical composition comprising a substantially sterile water-extract of Nerium species having an endotoxin concentration of less than about 150 units/mL, together with at least one pharmaceutically acceptable excipient therefor.
17. The pharmaceutical composition defined in claim 16, wherein the Nerium species comprises *Nerium oleander*.
18. The pharmaceutical composition defined in claim 16, wherein concentration of endotoxins in the extract is in the range of from about 20 units/mL to about 150 units/mL.
19. The pharmaceutical composition defined in claim 16, wherein concentration of endotoxins in the extract is in the range of from about 20 units/mL to about 120 units/mL.
20. The pharmaceutical composition defined in claim 16, wherein concentration of endotoxins in the extract is in the range of from about 20 units/mL to about 100 units/mL.
21. The pharmaceutical composition defined in claim 16, wherein concentration of endotoxins in the extract is in the range of from about 20 units/mL to about 80 units/mL.
22. The pharmaceutical composition defined in claim 16, wherein concentration of endotoxins in the extract is in the range of from about 20 units/mL to about 50 units/mL.
23. The pharmaceutical composition defined in claim 16, wherein the pharmaceutical composition is in the form of an injectable liquid.
24. The pharmaceutical composition defined in claim 16, wherein the pharmaceutical composition is in the form of a topical formulation.
25. The pharmaceutical composition defined in claim 24, wherein the topical formulation comprises a cream.
26. The pharmaceutical composition defined in claim 16, wherein the pharmaceutical formulation is in the form of an oral formulation.
27. The pharmaceutical composition defined in claim 26, wherein the oral formulation is selected from the group comprising tablets, caplets and capsules.
28. A process for producing a pharmaceutical composition comprising the steps of:
   (i) mixing a substantially sterile water-extract of Nerium species with at least one pharmaceutically acceptable excipient and water, the extract having an endotoxin concentration of less than about 150 units/mL; and
   (ii) drying the mixture produced in Step (i).
29. The process defined in claim 28, wherein the Nerium species comprises *Nerium oleander*.
30. The process defined in claim 28, wherein concentration of endotoxins in the extract is in the range of from about 20 units/mL to about 150 units/mL.
31. The process defined in claim 28, wherein concentration of endotoxins in the extract is in the range of from about 20 units/mL to about 120 units/mL.
32. The process defined in claim 28, wherein concentration of endotoxins in the extract is in the range of from about 20 units/mL to about 100 units/mL.
33. The process defined in claim 28, wherein concentration of endotoxins in the extract is in the range of from about 20 units/mL to about 80 units/mL.
34. The process defined in claim 28, wherein concentration of endotoxins in the extract is in the range of from about 20 units/mL to about 50 units/mL.
35. The process defined in claim 28, comprising the further step of reconstituting the dried pharmaceutical composition with a liquid carrier to produce an injectable liquid.
36. The process defined in claim 28, wherein the pH of the mixture during Step (i) is maintained in the range of from about 5 to about 8.
37. The process defined in claim 28, wherein the pH of the mixture during Step (i) is maintained in the range of from about 5 to about 7.
38. The process defined in claim 28, wherein Step (ii) comprises freeze-drying the mixture.
39. The process defined in claim 28, wherein Step (ii) comprises spray-drying the mixture.
40. The process defined in claim 28, wherein Step (ii) comprises at least one of heating and evaporating the mixture.

* * * * *